(12) United States Patent
Henning et al.

(10) Patent No.: US 6,537,243 B1
(45) Date of Patent: Mar. 25, 2003

(54) DEVICE AND METHOD FOR OBTAINING INTERSTITIAL FLUID FROM A PATIENT FOR DIAGNOSTIC TESTS

(75) Inventors: Timothy P. Henning, Vernon Hills, IL (US); Michael G. Lowery, Wildwood, IL (US)

(73) Assignee: Abbott Laboratories, Abbott Park, IL (US)

( * ) Notice: Subject to any disclaimer, the term of this patent is extended or adjusted under 35 U.S.C. 154(b) by 42 days.

(21) Appl. No.: 09/689,527

(22) Filed: Oct. 12, 2000

(51) Int. Cl.⁷ .................................. A61N 5/32
(52) U.S. Cl. ..................... 604/28; 600/581; 604/48; 604/93; 604/175; 604/180; 604/264; 604/290; 604/500; 604/507
(58) Field of Search ................. 604/264, 28, 48, 604/93, 128, 180, 175, 290, 500, 507; 600/581

(56) References Cited

U.S. PATENT DOCUMENTS

| | | | |
|---|---|---|---|
| 3,854,477 A | * 12/1974 | Smith | 604/175 X |
| 4,775,361 A | 10/1988 | Jacques et al. | |
| 4,854,322 A | * 8/1989 | Ash et al. | 604/48 X |
| 4,953,552 A | 9/1990 | DeMarzo | |
| 5,002,054 A | 3/1991 | Ash et al. | 600/581 X |
| 5,174,291 A | 12/1992 | Schoonen et al. | |
| 5,193,545 A | 3/1993 | Marsoner et al. | |
| 5,279,543 A | 1/1994 | Glikfeld et al. | |
| 5,362,307 A | 11/1994 | Guy et al. | |
| 5,423,803 A | 6/1995 | Tankovich et al. | |
| 5,730,714 A | 3/1998 | Guy et al. | |
| 5,746,217 A | 5/1998 | Erickson et al. | |
| 5,820,570 A | 10/1998 | Erickson et al. | |
| 5,951,521 A | * 9/1999 | Mastrototaro et al. | 604/180 X |
| 6,042,561 A | 3/2000 | Ash et al. | |

FOREIGN PATENT DOCUMENTS

| | | |
|---|---|---|
| EP | 0 513 789 | 11/1992 |
| EP | 0 722 288 | 7/1996 |
| WO | 94/13203 | 6/1994 |
| WO | 97/07734 | 3/1997 |

OTHER PUBLICATIONS

PCT International Search Report.
*Encyclopedia of Polymer Science and Engineering*, vol. 6, John Wiley & Sons, Inc. (New York: 1986), pp. 571–631.
Ito, et al., "A Novel Blood Glucose Monitoring System Based on an ISFET Biosensor and its Application to a Human 75 g Oral Glucose Tolerance Test", *Sensors and Actuators*, vol. B1, 1990, pp. 488–490.
Skragal, et al., "Portable System for On–line Continuous Ex Vivo Monitoring of Subcutaneous Tissue Glucose Using Open Tissue Perfusion", *Medical & Biological Engineering & Computing*, vol. 33, 1995, pp. 116–118.
Trajanoski, et al., "Open–flow Microperfusion of Subcutaneous Adipose Tissue for On–line Continuous Ex Vivo Measurement of Glucose Concentration", *Diabetes Care*, vol. 20, No. 7, 1997, pp. 1114–1121.

* cited by examiner

*Primary Examiner*—Gregory Huson
*Assistant Examiner*—Kathleen J. Prunner
(74) *Attorney, Agent, or Firm*—David L. Weinstein

(57) ABSTRACT

A device for obtaining a sample of interstitial fluid from a patient for use in monitoring the level of blood glucose in the patient. The device comprises a hollow tube having a wall surrounding a cavity, wherein the wall of the tube contains a multiplicity of pores.

18 Claims, 3 Drawing Sheets

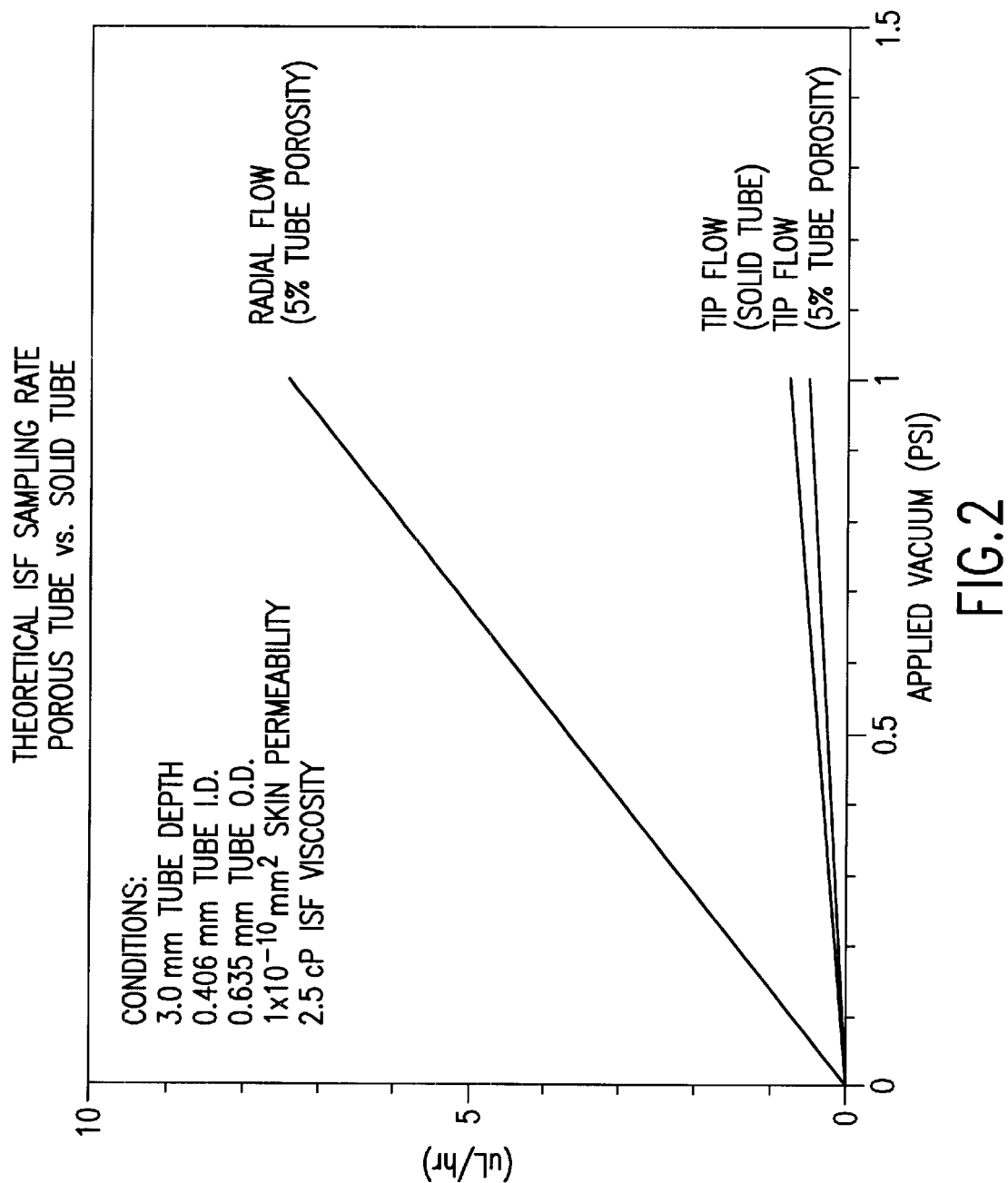

DEVICE AND METHOD FOR OBTAINING INTERSTITIAL FLUID FROM A PATIENT FOR DIAGNOSTIC TESTS

BACKGROUND OF THE INVENTION

1. Field of the Invention

This invention relates to a device and a method for obtaining interstitial fluid from the body of a patient for use in a diagnostic test. More particularly, this invention relates to a device and a method for obtaining interstitial fluid from the body of a patient at a rapid rate of collection.

2. Discussion of the Art

Interstitial fluid is the substantially clear, substantially colorless fluid found in the human body that occupies the space between the cells of the human body. Several methods have been used to obtain interstitial fluid from the body of a patient for diagnostic tests. Diagnostic tests that can be run with samples of interstitial fluid include, but are not limited to, glucose, creatinine, BUN, uric acid, magnesium, chloride, potassium, lactate, sodium, oxygen, carbon dioxide, triglyceride, and cholesterol.

It is much more difficult to obtain a sample of interstitial fluid from the body of a patient than it is to obtain a sample of blood from the body of a patient. Blood is pumped under pressure through blood vessels by the heart. Consequently, a cut in a blood vessel will naturally lead to blood flowing out of the cut because the blood is flowing under pressure. Interstitial fluid, which is not pumped through vessels in the body, is under a slight negative pressure. Moreover, the amount of interstitial fluid that can be obtained from a patient is small because this fluid only occupies the space between the cells of the human body. Currently available methods for obtaining large amounts of interstitial fluid are unsatisfactory, because these methods are accompanied by undesirable side effects.

Several methods have been employed to obtain access to interstitial fluid for glucose monitoring. These methods include, but are not limited to, microdialysis, heat poration, open flow microperfusion, ultrafiltration, subcutaneous implantation of a sensor, needle extraction, reverse iontophoresis, suction effusion, and ultrasound.

Microdialysis involves placing microdialysis tubes in the body, introducing a fluid into the tubes, allowing the fluid to traverse the length of tubing in the body, and withdrawing the fluid to a location outside the body. As the fluid passes through the microdialysis tubing in the body, glucose from the body is exchanged with the fluid inside the tubing, resulting in a change in glucose concentration primarily in the fluid inside the tubing. The change in the concentration of glucose in the tubing can be measured with a sensor that is external to the body.

There are several drawbacks in the use of microdialysis equipment for measuring the concentration of glucose. Microdialysis tubes have walls. The walls of the microdialysis tubes are formed from a material called dialysis membrane. This membrane allows molecules below a certain size to pass but restricts the movement of larger molecules. The amount of glucose that is exchanged may be small, leading to small changes in the concentration of glucose in the fluid inside the microdialysis tubing. These small changes in the concentration of glucose can be difficult to detect accurately. Moreover, the amount of time required for the fluid to circulate through the microdialysis tubes can be great. Accordingly, the concentration of glucose being measured by a sensor that is external to the body can lag behind the actual concentration of glucose inside the body by several minutes. Reducing the length of the tubing and increasing the rate of the pumping of the fluid can decrease the duration of this lag, but such actions also decrease the amount of glucose being transferred to the tubing. In addition, obtaining accurate measurements of the concentration of glucose from solutions having a low concentration of glucose is difficult. Furthermore, the microdialysis tubing can break off during use or upon withdrawal from the body, thereby presenting a hazard to the user. Finally, the exchange of glucose across the membrane of the tubing can vary over time, resulting in erroneous determinations of the concentration of glucose.

Heat generated by a light from a laser that acts upon a dye or heat generated by a heated wire can be used to form openings in the outermost layer of the skin, the stratum corneum. The formation of openings in the skin by means of heat is described in WO 97/07734. Interstitial fluid can be extracted from the openings in the skin by means of a vacuum or by application of pressure around the periphery of the openings. The use of a laser to form openings in the skin is expensive, because the laser must not only be powerful enough to cause the formation of the openings in the skin, but must also be properly focused to create small openings in the skin. A plurality of openings must be formed in the skin order to obtain a sufficient quantity of interstitial fluid. If one laser is used, the mechanism housing the laser will be complex and costly, on account of the necessity of additional components for moving the laser to a plurality of locations on the stratum corneum. Alternatively, a plurality of lasers could be incorporated into an instrument to form a plurality of openings in the stratum corneum. This approach would be costly because of the additional cost of extra lasers. Because of the limitations of the laser and because of unsightly discoloration caused by the formation of openings in the skin, the number of openings per each interstitial fluid extraction operation is typically limited to three to six. The amount of interstitial fluid extracted will be limited to the amount that can be drawn through these openings. A greater number of openings could provide an increased rate of collection of interstitial fluid, but a greater number of openings would be impractical. The openings would have to be distributed over a wide area of skin, thereby making the harvesting of the interstitial fluid difficult.

Open flow microperfusion is similar to microdialysis. A fluid flows through a tube placed in the body, and the fluid is exchanged between the body and the tube. The concentration of glucose in the fluid exiting the body is proportional to the concentration of glucose in the body. Typically, if the concentration of glucose in the fluid inside the tube is initially zero, by the time the fluid leaves the body, the concentration of glucose in the exiting fluid will be one-third that of the concentration of glucose in the body. The difference between open flow microperfusion and microdialysis resides in the type of tube used. Microdialysis tubes have very small pores that are designed to allow only small molecules to diffuse through the walls of the tube. Pore sizes in microdialysis tubing are typically on the order of 1 to 10 nm. Open flow microperfusion systems have pores typically on the order of 200 micrometers. In the case of open flow microperfusion, the pores should not restrict the movement of any molecules in the interstitial space. Neither the microdialysis method nor the open flow microperfusion method extracts a pure sample of interstitial fluid; accordingly, these methods require a calibration factor.

Ultrafiltration involves placing microdialysis tubing inside the body and extracting interstitial fluid from the body through the tubing by means of vacuum. A steady stream of fluid cannot be obtained because the application of vacuum leads to the formation of bubbles in the fluid. A lower level of vacuum would reduce bubble formation but would increase the amount of time required to remove the sample of interstitial fluid from the body and transfer it to a glucose detector. The pores of the microdialysis tubing become clogged over time, thereby leading to lower flow rates or the need to increase levels of vacuum. The interstitial fluid that is obtained does have concentrations of glucose similar to that found in blood, making the determination of the concentration of glucose more accurate than that of microdialysis. However, the length of tubing that must be inserted under the skin is typically on the order of centimeters in length. A typical patient cannot easily insert this length of tubing. Furthermore, the greater the length of the tubing, the more likely that it will break off during use or upon withdrawal from the body.

A sensor implanted beneath the skin can be used to monitor the concentration of glucose continuously. This type of sensor does not require removal of fluid from the body to measure the concentration of glucose. The sensor is difficult to calibrate because it is located inside the body. The only way to confirm the accuracy of the sensor is to measure blood glucose level by fingerstick methods. Furthermore, the sensor is subject to the motion of the body as well as to attacks by the body's immune system. The overall accuracy of these devices is usually poor.

A hollow needle can be placed in the dermis layer of the skin and used to extract interstitial fluid by means of vacuum or by means of pressure applied to the skin around the periphery of the needle. The amount of interstitial fluid withdrawn is usually very small, typically on the order of one microliter or less. Interstitial fluid can enter the needle only through the open end. If the needle is used for extended periods of time, it may cause irritation to the user. The level of vacuum required to obtain a steady flow of interstitial fluid may be high and bubble formation may be seen, similar to that seen in the case of ultrafiltration. If a low level of vacuum is used, the flow of interstitial fluid may be slow and the significant lag time may cause the concentration of glucose measured to differ significantly from the actual concentration of glucose.

Passing a small current through the skin has been used to drive drugs having low molecular weight through the skin. This process is known as iontophoresis. The passage of current can also cause ionic material from within the skin to be extracted from the body in a process called reverse iontophoresis. As the ionic materials move outside the body, they drag water with them as well as any non-ionic material dissolved in the water. By means of this technique, glucose can be removed from the body through the skin. However, the process is slow and the concentration of glucose extracted is low.

Suction effusion first employs adhesive tape to remove the outer layer of the skin. The tape must be applied to the skin several times, typically 20 to 100, until the outer layer of skin is removed. Once the outer layer of skin is removed, a vacuum is applied to suck interstitial fluid out through the area where the outer layer of skin was removed. Removing the outer layer of the skin is very time consuming, and the amount of interstitial fluid that can be sucked out by means of the vacuum is very small.

Ultrasound has been claimed to cause the skin to become more porous. After the skin is exposed to ultrasonic energy, interstitial fluid containing glucose may be extracted from the more porous skin by means of a vacuum. It has also been suggested that ultrasound can aid in the transport of fluid across the skin. The concentration of glucose in the extracted fluid can then be measured by means of a glucose detector. Experimental evidence does not show conclusively that ultrasound causes the skin to become more porous. The techniques described in the prior art either obtain very little interstitial fluid from the body or require extreme conditions, e.g., the application of very high vacuum levels, to extract the interstitial fluid. The techniques of the prior art also suffer from the shortcoming of extracting fluids containing low concentrations of glucose, which concentrations are difficult to measure accurately.

In view of the foregoing, it would be desirable to develop a technique for obtaining interstitial fluid from the body of a patient at a rapid rate of collection. It is desired that the technique provide a large amount of interstitial fluid, that the technique not be harmful to the patient, that the technique be of low cost, and that the technique provide a sample that produces accurate results.

SUMMARY OF THE INVENTION

In one aspect, this invention provides a device for obtaining a sample of interstitial fluid from a patient for use in monitoring the level of blood glucose in the patient. The device comprises a hollow tube having a wall, wherein the wall of the tube contains a multiplicity of pores.

The shape of the tube preferably corresponds to the shape of the device used to form the opening in the skin into which the tube is inserted. For example, if the device for forming the opening in the skin is cylindrical, such as, for example, a needle, the tube is preferably cylindrical in shape. The preferred shape of the tube is cylindrical. The shape of the tube determines the shapes of the openings at each end of the tube.

The tube should be of sufficient length so that a sufficient number of pores can be formed in the wall of the tube so the flow rate of the interstitial fluid would be equal to or greater than the flow rate required for using a commercially feasible assay. The tube should not be so long that an excessively long needle would be required to insert it, because the use of such a long needle would be painful to the patient.

The tube should be of sufficient diameter that the flow rate of interstitial fluid will be adequate for a commercially feasible assay. The diameter should not be so great that insertion of the needle required to form the opening in the skin for the tube will cause excessive pain to the patient. The smallest practical needle or lancet for forming an opening in the skin of a patient is 31 gauge. The outer diameter of a needle of 31 gauge is about 0.25 mm. Therefore, the inside diameter of the tube is preferably at least about 0.25 mm. The inside diameter of the tube is limited by the size of the largest needle or lancet that could comfortably be used to form the opening in the skin to insert the tube. A needle of 18 gauge (about 1.25 mm in diameter) is probably the largest needle that would be inserted into a patient. The inside diameter of the tube preferably does not exceed 1.25 mm.

The thickness of the wall of the tube should be sufficient to ensure mechanical stability. Typically, a wall thickness of from about 0.2 mm to about 0.5 mm is preferred. The outside diameter of the tube preferably does not exceed 2.25 mm. The outside diameter of the tube is preferably at least about 0.65 mm.

The size of the pores in the wall of the tube preferably exceeds the diameter of a red blood cell so that the pores will not be clogged by red blood cells. The maximum pore size is preferably less than the inside diameter of the tube in order to maintain the mechanical integrity of the tube. The number of pores will be based on the desired porosity of the tube and the size of the pores.

In another aspect, this invention provides an assembly for inserting the device into the skin of a patient. In still another aspect, this invention provides a method for employing the device of this invention for obtaining obtain interstitial fluid from the body of a patient.

The device of this invention can obtain interstitial fluid from the body of a patient at a rapid rate of collection. Moreover, the device can provide a large amount of interstitial fluid. In addition, the device and method for its use are not harmful to the patient. The device is inexpensive. Most importantly, the device helps to provide a sample that produces accurate results.

BRIEF DESCRIPTION OF THE DRAWINGS

FIG. 2 is a graph that compares rate of removal of interstitial fluid by means of this invention with rate of removal of interstitial fluid by means of a device of the prior art.

DETAILED DESCRIPTION

As used herein, the term "diameter" means the length of the longest straight line segment passing through the center of a figure, e. g., a circle or an ellipse, and terminating at the periphery. The term "multiplicity" means a large number.

Figure 1A:
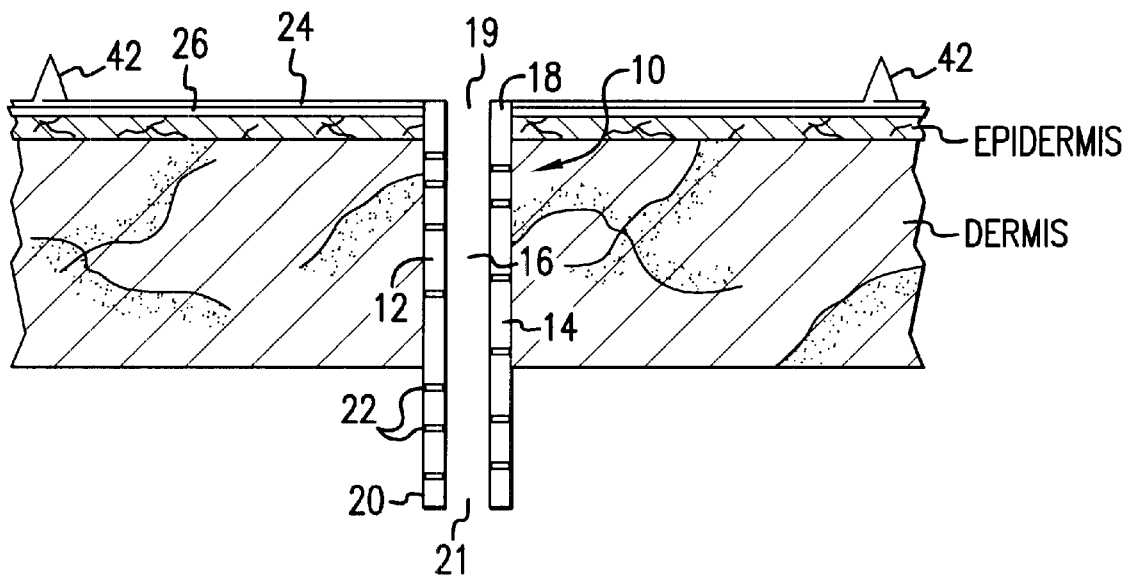
FIG. 1A is a schematic side view in elevation of a cross-section of the tube of the present invention. In this view, the needle holder and the analyte detector are not present.
Figure 1B:
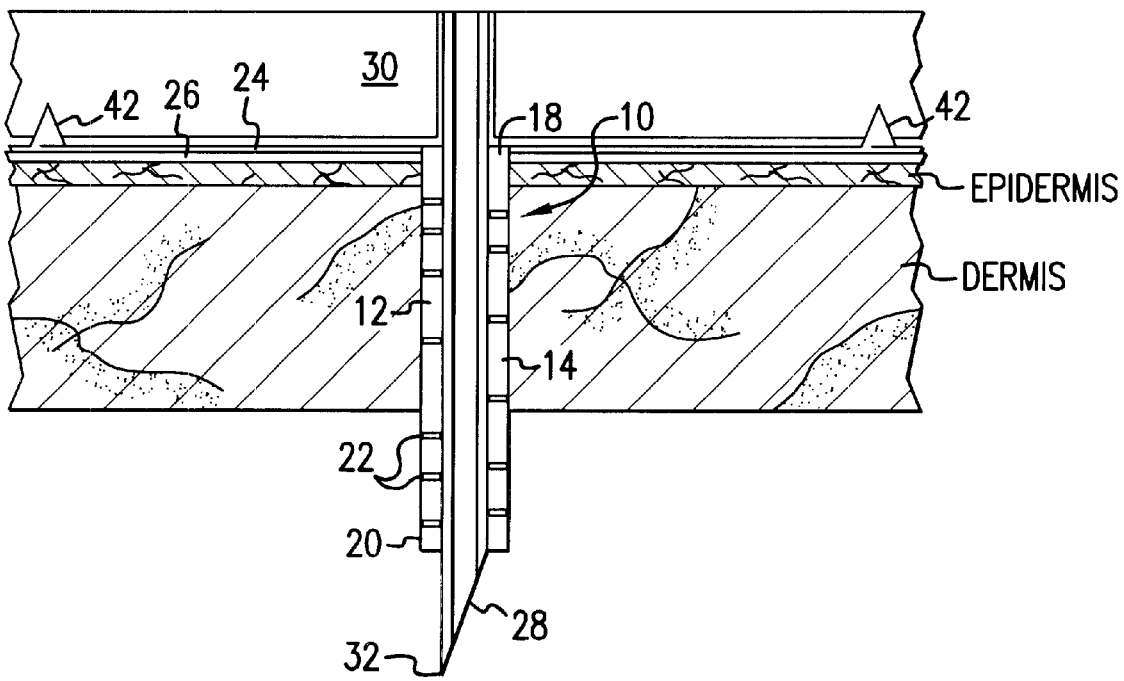
FIG. 1B is a schematic side view in elevation of a cross-section of the tube of the present invention. In this view, the needle holder is present.

Referring to FIGS. 1A and 1B, the device 10 of this invention comprises a hollow tube 12 comprising a wall 14 surrounding a cavity 16, a first end 18, which has an opening 19, and a second end 20, which has an, opening 21. A multiplicity of pores 22 is formed through the wall 14 of the tube 12. The second end 20 of the tube 12 is attached to a patch 24. The patch 24 has a layer 26 of adhesive on one major surface thereof for attaching the patch 24 to the surface of the skin of a patient. The shape of the tube 12 is not critical, but the tube is preferably cylindrical in shape. In the case of a cylindrical tube, the diameter of the tube 12 is typical of those tubes used for the administration of insulin to a patient by means of an insulin pump. An elongated element, such as, for example, a needle 28, can be used to aid in the insertion of the second end 20 of the tube 12 below the surface of the skin of a patient. The needle 28, which is held by a needle holder 30, can be placed in the hollow cavity 16 of the tube 12 by inserting the tip 32 of the needle into the opening 19 in the first end 18 of the tube 12. The diameter of the needle 28, which is cylindrical in shape, is typical of those needles used for administration of insulin to a patient by means of an insulin pump. The tip 32 of the needle 28 should project slightly beyond the opening 21 in the second end 20 of the tube 12 in order to facilitate insertion of the tube 12 into the skin of a patient.

The openings 19, 21 at the ends 18, 20 of the tube 12 are defined by the shape of the tube 12. A cylindrical tube, as shown in FIG. 1D, preferably has openings having the shape of a circle or an ellipse.

The needle 28 can also be in the shape of a blade. The tube 12 would then preferably have the shape of a parallelepiped, as shown in FIG. 1E, to fit closely around the outside of the blade-shaped needle. If the needle 28 has some other shape, cavity 16 of the tube 12 would preferably have a shape such that the interior surface of the wall 14 of the tube 12 would fit closely around the surface(s) of the needle 28.

The length of the tube 12 is preferably less than that of a tube typically used for the administration of insulin. A very long tube is not preferred because it would require a long needle to insert it. The use of a long needle would result in excessive pain to the user. Furthermore, a long tube does little to increase the rate of extraction of interstitial fluid from the skin. A very short tube would not allow an adequate number of pores to be placed in the wall of the tube, with the result that the increase in rate of extraction of interstitial fluid from the skin would be minimal.

The tube 12 should be of sufficient length to provide access to a large volume of interstitial fluid. When the length of the tube 12 is sufficient, a sufficient amount of interstitial fluid can be removed from the body at a sufficient rate to provide a sample of fluid that will yield a reading of the blood glucose level, for the patient in a timely manner. As stated previously, the tube 12 should not be too long in order to prevent discomfort to the patient. In addition, the tube 12 should not be too long in order to prevent the interstitial fluid that enters the opening 21 at the second end 20 of the tube 12 from lagging behind the interstitial fluid that enters the pores 22 of the tube 12 by several minutes. If the lag time were too long, the interstitial fluid reaching the glucose detector would not provide a reasonably accurate reading of the blood glucose level. A glucose detector suitable for use with the device of this invention is typically in the form of a sensor, of the type described in WO 94/13203, incorporated herein by reference. While this invention has been described with respect to monitoring the blood glucose level of a patient by means of a glucose detector, the device, assembly and method of this invention can be used to measure the concentration of analytes other than glucose. The tube 12 must not be so short that the wall 14 of the tube 12 has an insufficient number of pores to bring about in an increase in the rate of flow of interstitial fluid from the patient to the detector. The length of the tube 12 preferably ranges from about 2 mm to about 10 mm, more preferably from about 5 mm to about 10 mm.

If the needle 28 used to form the opening in the skin into which the tube 12 is inserted is cylindrical in shape, the cavity 16 of the tube 12 should be of sufficient diameter to accommodate the needle 28. The smallest practical needle or lancet is 31 gauge. The outer diameter of a needle of 31 gauge is about 0.25 mm. Therefore, the inside diameter of the tube 12 is preferably at least about 0.25 mm. The inside diameter of the tube is limited by the size of the largest needle that could be used to insert the tube 12 into the patient comfortably. A needle of 18 gauge (about 1.25 mm in diameter) is probably the largest needle that a patient would insert. The inside diameter of the tube 12 would preferably not exceed about 1.25 mm. If the needle 28 is of a shape other than cylindrical, the dimensions of the cavity 16 of the tube 12 should be of sufficient magnitude to accommodate the needle 28.

The minimum thickness of the wall 14 of the tube 12 is preferably about 0.1 mm. This minimum thickness would result in a minimum outside diameter of the tube 12 of about 0.45 mm. Thicker walls are preferable because they would result in a tube 12 having greater mechanical stability. The thickness of the wall 14 preferably ranges from about 0.1 mm to about 0.5 mm. The maximum thickness of the wall 12 would result in a maximum outside diameter of the tube 12 of about 2.25 mm.

The tube 12 can be made of any material suitable for use in the human body. Preferred materials are polymers. A preferred polymeric material for making the tube 12 is polytetrafluoroethylene (PTFE), because of biocompatibility and ease of insertion. The needle 28 is preferably made of steel.

The pores 22 should be sufficiently large that they do not easily become clogged. It is preferred that the pores 22 have a diameter greater than about five (5) micrometers so that any red blood cells released during insertion of the tube 12 can pass through the pores 22 in the wall 14 of the tube 12. The upper limit of pore diameter depends on the diameter of the tube 12 and the materials of construction of the tube 12. A typical tube suitable for insulin delivery has a diameter of 0.635 mm and a circumference of 2.0 mm. The diameters of the pores 22 should preferably be smaller than one-fourth the circumference of the tube 12 so that the tube 12 will display sufficient physical integrity for the purpose of this invention. A tube that is 0.635 mm in diameter should have pores having a diameter of less than about 0.5 mm. The percentage of the surface of the tube 12 containing pores 22 can vary. The largest inside diameter of the tube is expected to be 1.25 mm so the maximum pore diameter preferably does not exceed 1 mm. As stated previously, the lower limit of pore diameter is preferably, not less than 5 micrometers. If the percentage of the surface of the tube 12 containing pores 22 is too low, the benefit of having pores will not be realized. If the percentage of the surface of the tube 12 containing pores 22 is too high, the physical integrity of the tube will be compromised.

The porosity of the walls 14 of the tube 12 preferably varies from about, 1% to about 10% in order to maintain the structural integrity of the tube 12. The pore count would then vary from about 10 to about 10,000 pores. per mm of tube length.

The tubes 12 themselves can be prepared by means of an extrusion process. Extrusion processes are known to those having skill in the art and are described, for example, in *Encyclopedia of Polymer Science and Engineering,* Volume 6, John Wiley & Sons, Inc. (1986), pp. 571-631, incorporated herein by reference. The pores 20 in the wall 14 of the tube 12 can be formed by laser drilling, radiation etching, molding, or any other technique suitable for forming openings in the walls of polymeric material.

The tube 12 must be easily removable in one piece from the body after being implanted for several days. Remnants of the tube 12 cannot be allowed to remain inside the body for the reason that such remnants could bring about infection of the patient.

OPERATION

Figure 1C:
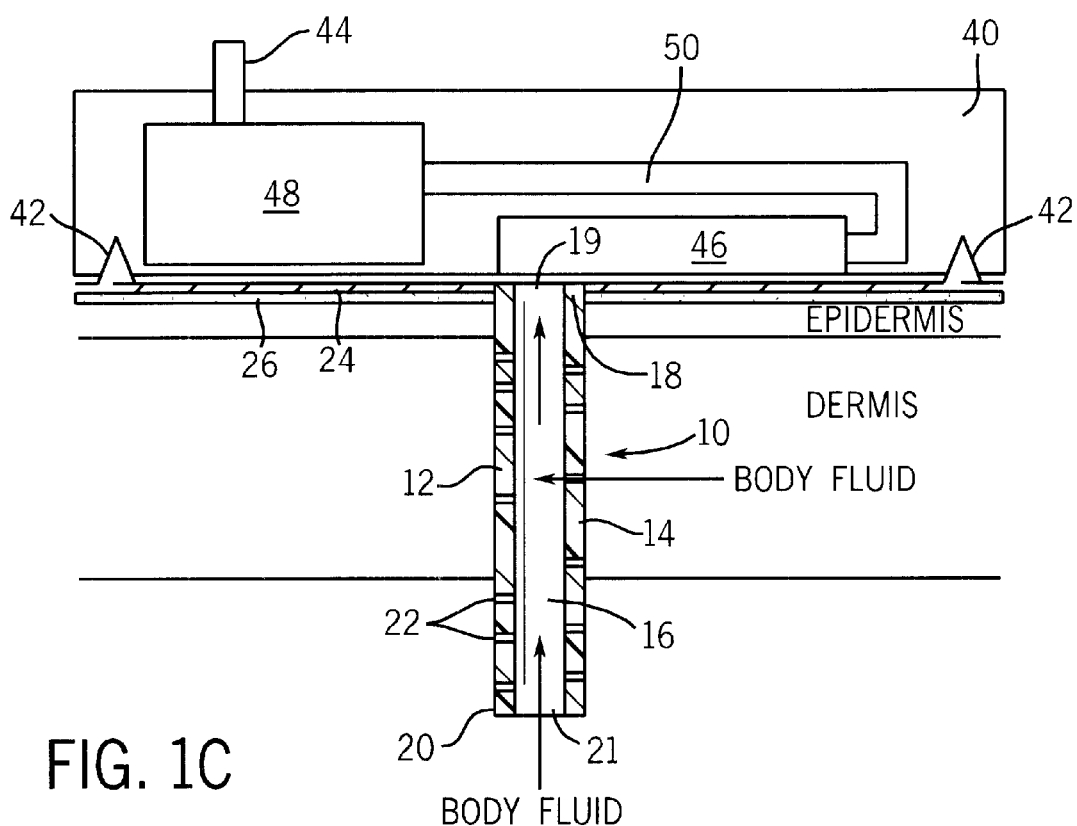
FIG. 1C is a schematic side view in elevation of a cross-section of the tube of the present invention. In this view, the needle holder is absent, and a glucose detector is present.
Figure 1D:
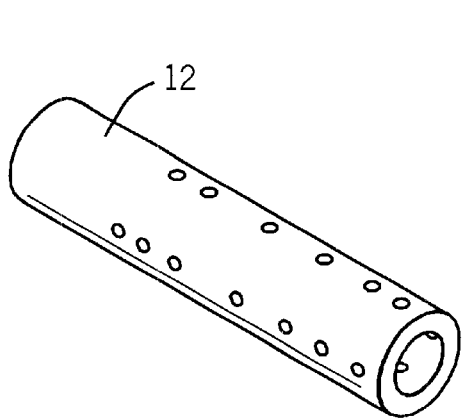
FIG. 1D is a perspective view of the cylindrical embodiment of the tube of the present invention.
Figure 1E:
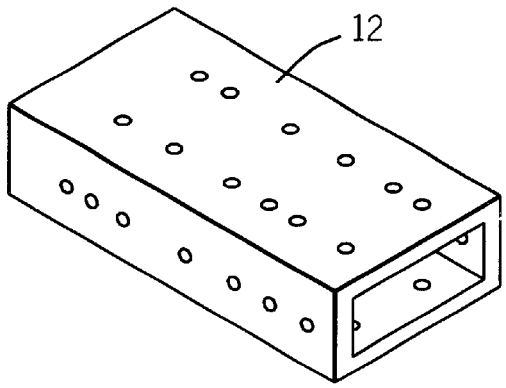
FIG. 1E is a perspective view of the tube of the parallelepiped embodiment of the tube of the present invention.

The operation of the invention is shown in FIGS. 1A, 1B, and 1C. The needle 28, which is held by the needle holder 30, is inserted into the cavity 16 of the tube 12 of the device 10 via the opening 19 in the first end 18. The needle 28 and the tube 12 surrounding the needle 28 are inserted into the skin. The patch 24 is firmly attached to the surface of the skin by means of the adhesive of layer 26. The needle 28 is then removed from the cavity 16 of the tube 12 by means of removing the needle holder 30. A detector holder 40 is attached in the position where the needle holder 30 had been formerly attached. Alignment guides 42 aid in the proper alignment of the detector holder 40. The detector holder 40 is attached to a source of vacuum by means of a tubular connector 44. Alternatively, the source of vacuum could be miniaturized so that it would become part of the detector holder 40. The application of vacuum causes interstitial fluid to be drawn out of the body and into contact with a detector 46 (e. g., a glucose detector), which contains reagents that react with the analyte (e. g., glucose) in the interstitial fluid. The interstitial fluid is collected in a waste chamber 48 after the detector 46 has received a sufficient amount of interstitial fluid to carry out an assay. A connecting tube 50 connects the glucose detector 46 with the waste chamber 48. The interstitial fluid flows into the tube 12 through the pores 20 in the wall 14 of the tube 12 and through the opening 21 in the end 20 of the tube 12.

The presence of pores 22 in the wall 14 of the tube 12 brings about a large increase in the amount of interstitial fluid that can be withdrawn at a given level of vacuum. A comparison of the amount of fluid that can be extracted as a function of level of vacuum applied is shown in FIG. 2. The model is based on published data relating to skin permeability and viscosity of interstitial fluid. FIG. 2 shows that there is a nearly 10-fold increase in the rate of extraction of interstitial fluid by using the tube 12 of this invention as compared with a tube of the prior art. The tube of the prior art has no pores in the wall thereof.

The increased rates of extraction of interstitial fluid would result in lower lag time between glucose concentration values obtained from whole blood samples and glucose concentration values obtained from samples of interstitial fluid. The increased rate of extraction of interstitial fluid would also enable the use of glucose detectors that require a greater volume of interstitial fluid for determining glucose concentration. Such detectors are easier to develop and manufacture than are detectors that must utilize a very small volume of interstitial fluid. The level of vacuum could be decreased when the tube of this invention is used, thereby allowing the use of smaller vacuum pumps. The use of smaller vacuum pumps could enable the size of a glucose monitoring device to be reduced to the size of a wrist watch.

Heat poration, reverse iontophoresis, and ultrasound all require complex and expensive instrumentation to increase porosity of the skin. Heat poration, ultrafiltration, suction effusion fluid, and ultrasonic energy require a strong vacuum to extract fluid from the skin.

Microdialysis, open flow microperfusion, reverse iontophoresis, and ultrasound all measure fluid samples that have been diluted. Such diluted samples present two challenges for making accurate measurements of glucose concentration. First, the low concentration of glucose present in the extracted sample is more difficult to measure because noise will tend to overwhelm the glucose signal. Second, the amount of glucose extracted will vary over time, with the result that accuracy of measurement will decrease or the frequency of calibration will have to be increased in order to compensate for variations in volume of glucose extracted.

Microdialysis, heat poration, open flow microperfusion, ultrafiltration, reverse iontophoresis, suction effusion, and ultrasonic energy require a significant amount of time to withdraw a sample of interstitial fluid. Accordingly, these methods result in a lag time (delay) between the actual blood glucose level and the blood glucose level obtained by means of analysis of interstitial fluid. Heat poration, ultrafiltration, needle extraction, and suction effusion all remove very small amounts of interstitial fluid. They all require glucose detectors that are very small, which are not commercially available.

Subcutaneous implanted sensors cannot be calibrated once they are placed in the body. A pseudo calibration can be performed with a fingerstick glucose measurement, but an accurate calibration cannot be performed, because an accurate calibration would require that the glucose detector be placed in a calibration solution. This type of calibration cannot be carried out because the glucose detector is inside the body.

Various modifications and alterations of this invention will become apparent to those skilled in the art without departing from the scope and spirit of this invention, and it should be understood that this invention is not to be unduly limited to the illustrative embodiments set forth herein.

What is claimed is:

1. An assembly for obtaining fluid from an opening formed in the skin of a patient comprising:
   (a) a device suitable for use in withdrawing fluid from an opening formed in the skin of a patient, said device comprising a hollow tube comprising a wall surrounding a cavity, said hollow tube having a first end and a second end, said wall running from said first end to said second end, said wall having a multiplicity of pores formed therein;
   (b) an elongated element capable of forming said opening in said skin, said elongated element capable of being inserted in said first end of said hollow tube and projecting beyond said second end of said tube.

2. The assembly of claim 1, wherein said wall of said tube comprises a polymeric material.

3. The assembly of claim 1, wherein said tube has a length ranging from about 2 mm to about 10 mm.

4. The assembly of claim 1, wherein said tube has a length ranging from about 5 mm to about 10 mm.

5. The assembly of claim 1, wherein said tube is cylindrical in shape.

6. The assembly of claim 5, wherein the inside diameter of said tube is at least about 0.25 mm but the inside diameter of said tube does not exceed about 1.25 mm.

7. The assembly of claim 5, wherein said tube has an outside diameter ranging from a minimum outside diameter of about 0.45 mm to a maximum outside diameter of about 2.25 mm.

8. The assembly of claim 5, wherein a maximum pore size is less than the inside diameter of the tube.

9. The assembly of claim 1, wherein said tube is in the shape of a parallelepiped.

10. The assembly of claim 1, wherein said wall of said tube has a porosity of from about 1% to about 10%.

11. The assembly of claim 1, wherein the number of pores per mm of tube length ranges from about 10 to about 10,000.

12. The assembly of claim 1, wherein a maximum pore diameter does not exceed 1 mm and a lower limit of pore diameter is not less than 5 micrometers.

13. The assembly of claim 1, further including a patch bearing a layer of adhesive on one major surface thereof for adhering said assembly to said skin.

14. The assembly of claim 1, further including a holder for said elongated element.

15. The assembly of claim 1, further including guides for aligning a detector holder.

16. A method for obtaining interstitial fluid from the body of a patient, said method comprising the steps of:
   (a) providing the assembly of claim 1, said tube surrounding said elongated element;
   (b) inserting said elongated element and said tube surrounding said elongated element into said body of said patient;
   (c) removing said elongated element from said cavity of said tube; and
   (d) collecting interstitial fluid from said body of said patient, said interstitial fluid exiting from said first end of said tube.

17. The method of claim 16, further including the step of determining the blood glucose level from said collected interstitial fluid.

18. The method of claim 16, wherein said interstitial fluid is collected with the aid of vacuum.

* * * * *